United States Patent [19]

Matkovich et al.

[11] Patent Number: 4,828,386
[45] Date of Patent: May 9, 1989

[54] MULTIWELL PLATES CONTAINING MEMBRANE INSERTS

[75] Inventors: Vlado I. Matkovich, Glen Cove; Peter J. Degen, Huntington, both of N.Y.

[73] Assignee: Pall Corporation, Glen Cove, N.Y.

[21] Appl. No.: 64,342

[22] Filed: Jun. 19, 1987

[51] Int. Cl.[4] ............................................. G01N 21/03
[52] U.S. Cl. ...................................... 356/246; 436/809
[58] Field of Search ................ 356/246; 436/524, 531, 436/809

[56] References Cited

U.S. PATENT DOCUMENTS 3,027,799  4/1962  Weichselbaum .................... 356/246
4,146,365  3/1979  Kay et al. ........................ 436/809 X
4,290,997  9/1981  Souvaniemi ...................... 356/246 X
4,357,142 11/1982  Schall, Jr. et al. ................. 436/531
4,629,563 12/1986  Wrasidlo ........................ 210/500.34

Primary Examiner—Vincent P. McGraw
Attorney, Agent, or Firm—Leydig, Voit & Mayer

[57] ABSTRACT

A multiwell plate suitable for use in a spectrometer which uses a vertical beam of light comprising a first plate having a plurality of wells for receiving sample, wherein the wells have transparent bottom surfaces to allow for the transmission of a vertical beam of light, and a unitary insert comprising a biochemically compatible microporous surface capable of binding biological materials shaped to fit into at least one well of the plate without interfering with the vertical beam of light.

20 Claims, 1 Drawing Sheet

MULTIWELL PLATES CONTAINING MEMBRANE INSERTS

FIELD OF THE INVENTION

The present invention relates to multiwell plates, such as the so-called microtiter plate, particularly multiwell plates designed for use with vertical beam spectrophotometry.

BACKGROUND

A number of diagnostic assays are carried out in automated equipment using multiwell plastic plates and automated equipment in which a vertical beam of light is used in making spectrophotometric readings in the individual wells of the plates. These plates have several common features: plastic wells with optically transparent bottom is isolated from one another with respect to liquid contained therein but physically connected in a precise geometric pattern. The wells are typically part of a plastic carrier plate, and the automated equipment is designed to have a movable stage into which one or more multiwell plates precisely fit. Most commonly these multiwell plates contain 96 wells arranged in an 8×12 pattern, although plates containing other numbers of wells are also available.

One common use of multiwell plates is in an automated diagnostic assay using antibodies to bind an analyte in a sample added to one or more of the wells of the plate. Before a multiwell plate can be used for this type of test, it must be coated with the appropriate antibody. This is normally accomplished by the user and consists of adding an antibody solution to the individual wells, followed by incubating and removing excess solution. During the incubation interval, the antibody binds non-convalently to the wall and bottom of the individual wells. The amount of antibody and the tenacity of the bond that the antibody makes to the walls of the individual wells are important factors in the sensitivity and reliability of the diagnostic test that uses the multiwell plate.

When antibody-coated plates are used in an automated, vertical beam spectrophotometer, samples are added to the individual wells. The plate is then placed in the movable stage of the spectrophotometer. Activating the machine causes the stage to automatically advance into the machine, and a series of preprogrammed steps occur. In a number of machines, hollow needles descend into some or all of the wells and either inject a liquid containing reagents used in the assay or remove a liquid from a previous step. The stage then shifts sufficiently to allow the process to be repeated in the next group of wells. After the last chemical step of the sequence, which typically results in the formation of a colored product, the stage shifts to a new location so that the individual wells are placed in proper register either above or below a light source which passes a beam of light vertically through the well to a detector which measures the amount of transmitted light of a particular wavelength. This reading is converted automatically to a reading of the amount of analyte present in the sample, since the amount of color formed in the reaction is related to the amount of analyte.

The chemical and biochemical reactions that eventually result in color formation take place at the surfaces of the individual wells. Specifically, it is the surface area of the well wetted by the antibody solution initially used to coat the wells that sets the maximum level of antibody which can be bound. Since the geometry of the individual wells is essentially fixed by the constraints of the automated equipment, there is a practical limit to antibody adsorption on typical multiwell plates in current use. This can cause falsely low readings when large amounts of analyte are present, since not enough antibody will be present on the well walls to bind all of the analyte, as well as problems in sensitivity.

One attempt to overcome this limitation has employed porous latex beads contained in the wells. The antibody is bound to the latex, and the well simply becomes a chamber containing the beads.

While this approach does provide a significant increase in bound antibody, it suffers from serious practical problems. For example, the beads are typically unconstrained and can be removed accidently during the filling and emptying cycles in the automated equipment. Tests utilizing beads are therefore more sensitive to slight variations in machine fill and empty cycles than are multiwell plates that do not contain beads.

A second problem with current multiwell devices relates to the tenacity of antibody binding to well walls. Since the adsorption of antibody is basically passive (i.e., hydrophobic) in current multiwell plates, slight differences in surface characteristics from well to well can provide significant differences in the amount of antibody bound. These variations can significantly effect the reliability of diagnostic assays that utilize antibody-coated multiwell plates. Although the use of antibodies bound to latex beads avoids this problem, the latex beads are subject to the problems discussed above.

Accordingly, there remains a need for improvements in multiwell plates to provide for increased antibody binding in a more reliable manner.

SUMMARY OF THE INVENTION

The present invention provides a multiwell plate suitable for use in a spectrophotometer which uses a vertical beam of light, comprising a first plate having a plurality of wells for receiving sample, wherein the wells have transparent bottom surfaces to allow for the transmission of the vertical beam of light, and a unitary insert comprising a biochemically compatible microporous surface capable of binding antibody shaped to fit into at least one well of the plate without interfering with the vertical beam of light.

BRIEF DESCRIPTION OF THE DRAWINGS

The present invention will be better understood by reference to the following detailed description when considered in combination with the figures that form part of this specification, wherein.

DESCRIPTION OF SPECIFIC EMBODIMENTS

Figure 1:
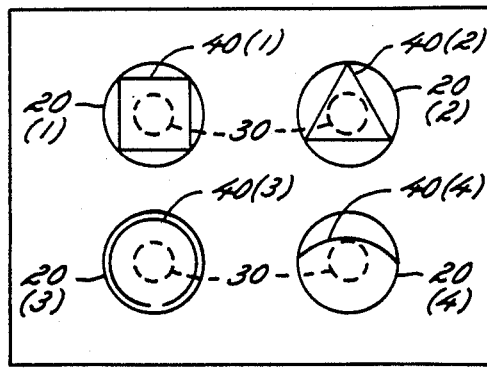
FIG. 1 is a plan view of a 4-well multiwell plate containing four different configurations of inserts.

The present invention provides a multiwell plate suitable for use in a spectrophotometer that uses a vertical beam of light but showing superior characteristics in binding antibody and other substances of biological origin. The basic multiwell plate resembles known multiwell plates in that it comprises a first plate having a plurality of wells for receiving sample affixed to or formed as part of the plate. These wells have transparent bottom surfaces to allow for the transmission of a vertical beam of light through the well and any sample that is contained therein. Superior capacity for the binding of biological substances is obtained by providing a unitary insert comprising a biochemically compatible microporous surface capable of binding antibody and/or other substances of interest for carrying out binding assays that is shaped to fit into at least one well of the plate without interfering with the vertical beam of light.

The inserts of the invention can fit either entirely within the wells of the microtiter plates or can extend above the well walls. Variations are also possible in the removability of the insert, the height of the microporous surface above the bottom of the well, the use of a backing material to support the microporous surface (the backing material being either rigid or flexible, porous or non-porous), and the composition of the microporous surface. However, the inserts are unitary; i.e., they may be inserted and/or removed from one or more wells as a unit. Accordingly, beads or other non-unitary inserts are not a part of the present invention. However, the inserts can be formed from multiple parts which are joined together to form the final unitary insert.

The configuration of the multiwell plate itself is not important to the present invention, and any of the known configurations can be used. These include unitary devices formed by an injection molding or other type of plastic-forming process. The wells can either comprise cylinders or other hollow shapes extending above the main surface of the plate that connects the wells together (the plate serving as the bottom surface of the individual wells) or the wells can comprise cylinders or other hollow shapes extending below the surface of the connecting plate, in which case the bottom surfaces of the wells can be either individually formed or formed from a lower transparent plate that interconnects the bottom surfaces of the individual wells. A number of different variations are available from commercial supply houses and can be readily adapted to form a plate of the present invention by use of the inserts described below.

The inserts of the invention will comprise at least one biochemically compatible microporous surface capable of binding antibody and other biological substances used in binding assays.

The invention can be practiced with any type of microporous binding surface (often called a reaction substrate or solid support). The phrase binding surface or reaction substrate is used here to indicate a material to which one or more of the reactants utilized in the assay is attached, whether such attachment is by a chemical bond or a physical process (such as adsorption). Although the bound material is usually an antibody or antigen, any reference herein to a binding surface capable of binding an antibody (or similar language) is not limiting or to be considered as indicating that only an antibody can be bound to the surface. Specific examples of molecules that participate in binding interactions suitable for use in assays of the type described here are set forth later in this specification. Preparation and use of solid supports per se in binding assays do not themselves constitute a part of the present invention since the preparation and use of such reaction substrates are well known. Rather, the present invention is concerned with the combination of such surfaces in particular configurations with multiwell plates that can be used in vertical beam photometry. Nevertheless, a brief description of reaction substrates is provided for completeness.

The particular material from which the binding surface is formed must not react adversely with substances found in either the samples, reagents, or solvents employed in the analyses. Preferred substrates will be formed from a liquophilic, microporous membrane or other porous material, typically having an absolute pore rating of about 0.001 to about 20 microns, preferably about 0.02 to about 8 microns, and most preferably about 0.2 to about 3 microns. The substrate preferably is also skinless. Materials which are suitable for use as the substrate also have voids volumes in the range of about 60–90%, preferably in the range of about 75–90%. Preferred materials are hydrophilic in nature and are therefore easily water-wettable and tend to freely pass and adsorb aqueous solutions. Polyamide binding surfaces are preferred. Nylon 66 is a preferred polyamide.

Liquophilicity, as used herein, refers to the wettability of the membrane by the liquid(s) with which it is contacted. The wettability or liquophilicity of a solid structure is a function of that structure's critical surface energy and the surface tension of the applied liquid. If the critical surface energy is at least as high as the surface tension of the liquid, the liquid will spontaneously wet the solid structure. For example, a microporous membrane having a critical surface energy of 72 dynes/cm or higher will be wetted by water, which has a surface tension of 72 dynes/cm; i.e., it is hydrophilic.

The capability of a porous structure (membrane or otherwise) to be wetted by a liquid can be determined by placing a drop of liquid on the porous structure. The angle of contact provides a quantitative measure of wetting. A very high angle of contact indicates poor wetting, while a zero angle of contact defines complete or perfect wetting. Materials used in the subject invention as the wettable or liquophilic porous substrate are characterized by being readily or spontaneously wetted by the applied liquid and have a low angle of contact with the applied liquid. Indeed, when a drop of a test liquid(s) is placed on a spontaneously wettable or liquophilic microporous substrate, the drop of liquid penetrates and wets the substrate, effectively providing a zero angle of contact therewith.

Wettability may also be expressed in terms of intrusion pressure which is defined as the applied pressure required for liquid to penetrate into the pores of the substrate. Materials which are particularly preferred for the substrate have intrusion pressures of or close to zero when water is the liquid.

Suitable material should also be capable of being treated with a retaining or immobilizing a substance being analyzed and/or a reactant which may be used to perform a specified test or reaction with the substance being analyzed for in a sample. The reactant, which may be of ionic, molecular, or macromolecular nature, may be immobilized on the reaction layer by strong physical forces or by being bonded in some manner, such as covalent chemical coupling, to the surface of the reaction layer. As employed herein, the term "surface" or "surface area" refers not only to the gross surface(s) of the structure but also, in those cases where a microporous structure such as a membrane is under consideration, to the surfaces of the micropores, i.e., the interior surfaces of the structure which are contacted by fluid during use.

Materials which are preferred for the reaction substrate have large surface areas. This feature permits a greater amount or higher concentration of reactant to be immobilized in the substrate. Accordingly, higher sensitivities and/or higher capacities may be achieved.

Some of the materials which are suitable or preferred for use as the substrate in the present invention are intrinsically hydrophilic or water-wettable. Others may be modified to render them hydrophilic. For example, BIODYNE ® is an N66 polyamide, microporous membrane commercially available from Pall Corporation which is inherently water-wettable by virtue of its method of manufacture (see U. S. Pat. No. 4,340,479).

Polyamides preferred for use in the present invention include nylons of the type described in U.S. Pat. No. 4,340,479, which is incorporated herein by reference. Another preferred membrane useful as the reaction layer is IMMUNODYNE TM, available from Pall Corporation. IMMUNODYNE TM is a modified CARBOXYDYNE ® membrane, also available from Pall Corporation. CARBOXYDYNE ® is a hydrophilic, microporous, skinless nylon 66 membrane with controlled surface properties formed by the cocasting process described in U.S. Pat. application Ser. No. 850,061, as discussed below, specifically by cocasting nylon 66 and a polymer containing an abundance of carboxyl groups to form a membrane having controlled surface properties characterized by carboxyl functional groups at its surfaces. IMMUNODYNE TM membranes may be prepared from CARBOXYDYNE ® membranes by treating them with trichloro-s-triazine in the manner described in U.S. patent application Ser. No. 642,899, discussed below.

Also included among the preferred polyamide membranes for the present invention are hydrophilic, microporous, skinless polyamide membranes with controlled surface properties of the type described in (1) U.S. patent application Ser. No. 850,061, filed Apr. 7, 1986, which is a continuation application of U.S. patent application Ser. No. 459,956, filed Jan. 21, 1983, which in turn is a continuation-in-part application of U.S. patent application Ser. No. 346,118, filed Feb. 5, 1982, and in (2) U.S. patent application Ser. No. 848,911, filed Apr. 7, 1986, which is a continuation application of U.S. patent application Ser. No. 460,019, filed Jan. 2, 1983, which is a continuation-in-part application of U.S. patent. application Ser. No. 346,119, filed Feb. 5, 1982.

All of the aforementioned U.S. patent applications are specifically incorporated herein by reference. These hydrophilic, microporous, substantially alcohol-insoluble polyamide membranes with controlled surface properties are formed by cocasting an alcoholinsoluble polyamide resin with a water-soluble, membrane-surface-modifying polymer having functional polar groups. Like the preferred hydrophilic, microporous nylon membranes which do not have controlled surfacemodified polar groups present, the polyamide membranes having controlled surface properties are also skinless; that is, they are characterized by through pores extending from surface-to-surface which are of substantially uniform size and shape. If desired, however, materials having tapered through pores, i.e., pores which are larger at one surface of the sheet, narrowing as they approach the opposite surface of the sheet, may be used.

The surface-modifying polymers used to prepare the polyamide membranes with controlled surface properties comprise polymers which contain substantial proportions of chemical functional groups, such as hydroxyl, carboxyl, amine, and imine groups. As a result, the membranes include, at their surfaces, high concentrations of functional groups such as hydroxyl, carboxyl, imine, or a combination of any of the above groups which do not react with one another. These polyamide membranes having controlled surface properties have higher concentrations of carboxyl or imine groups at their surfaces than the preferred microporous, hydrophilic, skinless polyamide membranes described above which do not have controlled surface properties, i.e., those which are formed from the preferred polyamide resin but are not cocast with surface-modifying polymer.

The substrate may be treated by any method known to one of skill in the art to deposit and/or bind reagents thereto. Treatment of the substrate with a suitable reagent(s) may be performed at the time at which diagnostic tests are to be performed, including addition of the test reagent(s) both immediately preceding and following introduction of the sample containing the analyte, or the substrate can be pretreated with at least one test reagent. Typically, pretreatment is conducted after the substrate has been prepared but before the device is shipped to a user.

A useful method of binding reagents of a molecular nature, especially macromolecules, and particularly those of a biological nature, is disclosed in U.S. patent application Ser. No. 642,899, filed Aug. 21, 1984, and specifically incorporated herein by reference. This application describes a method for immobilizing a wise range of biologically active substances on active nylon surfaces. In the application the reagent bound to the surface is referred to as an acceptor. The acceptor-bound surfaces described in the application are capable of immobilizing and binding a wide variety of biologically-active compounds, specifically ligands, to the acceptor molecules. Using such reaction layers permits the testing of bodily fluids, such as blood, serum, plasma, urine, saliva, and the like, and testing for particular substances by chemical assays or immunosassays that use a fluoroescent label. The macromolecules used as reagents and bound to the substrate or which are assayed for using the device of the present invention generally include materials of a biological nature and are frequently proteinaceous in nature. The reagent or acceptor molecule bound directly to the reaction substrate or the ligand being tested for include such substances as immunoglobulins or antibodies, either polyclonal or monoclonal, antigenic substances, apoproteins, receptors, glycoproteins, lectins, carbohydrates, hormones, enzymes, carrier proteins, heparin, coagulation factors, enzyme substrates, inhibitors, cofactors, nucleic acids, etc.

The microporous reaction surface can be utilized by itself, be applied to a rigid or flexible backing to form a layered insert, or be attached to or form part of a larger insert. Preferred backing are prepared from the same basic material as the microporous reaction/binding surface in order to provide compatible materials for attaching together. For example, a solid nylon backing can be provided for a microporous nylon surface. However, any combination of materials can be used as long as the attaching process does not adversely affect the binding properties of the microporous surface to an unacceptable degree.

Whether the microporous surface forms the entire insert or only part thereof, it is preferred that the microporous surface of the insert reside, when in use, in a lower portion of the multiwell plate well in order that the microporous surface is immersed completely within the liquid reaction medium. If a microporous surface extends above the liquid surface, capillary action within the pores will tend to draw reaction fluids into the portion of the microporous surface above the liquid surface. Removal of the liquid reaction medium followed by addition of a second medium will typically result in further wicking of the second liquid. For example, if the second liquid is a wash solution, rather than washing out the first liquid wicked into the upper portion of the microporous surface, the washed solution will merely push the first liquid higher or, if capillarity is exhausted, will not affect the liquid retained in the upper portion of the microporous surface. Accordingly, it is preferred that the microporous surface extend in the well no higher than the maximum height intended for liquid. This maximum vertical height is typically less than two-thirds, preferably less than one-half, and most preferably less than one-quarter of the height of the vertical walls of the well. If a microporous insert of the type that fits entirely within the well is utilized, the insert can reside on the bottom surface of the well and extend upward to the heights indicated above. If the microporous surface is part of a larger insert that fits only partly within the well, it is preferred that the microporous surface be on the lower portion of the insert so that it resides within the lower portion of the well as described above.

A principal characteristic of an insert of the invention is that it is shaped to fit into the well without interfering with the vertical beam of light from a vertical beam spectrophotometer or that it is easily removable to avoid interferring with the light beam during the measurement step. This beam of light typically passes through the center of the well. Accordingly, configurations for inserts that maintain all surfaces outside the central portion of the well are preferred. Typically, the vertical beam of light has a diameter less than one-half, preferably less than one-quarter, of the diameter of the well and is centered on the well. Accordingly, the unitary insert should be shaped so as to avoid interfering with this portion of the center of the well. However, it is interference with transmission of light, particularly light of the wavelength being measured, that is important, and some embodiments of the invention comprise transparent supports, connecting pieces, and the like (such as the top or bottom of a closed cylinder) that traverse this central portion of the reaction well. However, preferred embodiments of the invention do not interfere in any manner with the central portion of the well.

The geometry of the insert can be varied significantly and still fall within the scope of the present invention. For example, a rectangular sheet of microporous material slightly longer than the diameter of the well can be inserted fully into the well. If the microporous material is flexible and resilient, or is backed by a resilient material, the two ends of the insert will press against the vertical walls of the well and will slightly bow the sheet of microporous material. This bowing action removes the sheet from the center of the well. If the length of the microporous material is increased so that it is substantially equal in length to the circumference of the well, the sheet can be formed into the shape of an open cylinder and inserted into the well, where the sheet will fit against the vertical walls of the well. Providing a flexible and resilient microporous material (or microporous material affixed to a flexible and resilient backing) will result in a snug fit in the well as the cylinder tries to expand to its original flat shape.

In addition to curved inserts as discussed above, it is also possible to form flat sheets of microporous material into hollow polyhedrons without a top or bottom surface. For example, three sheets or a continuous folded surface of microporous material can be formed into the shape of a hollow prism or four sheets or a continuous folded surface of microporous material can be formed in the shape of a hollow cube. The sides of the polyhedrons are selected so that the corners of the inserts just touch the vertical walls of the well. Accordingly, light passes undisturbed through the central portion of the well.

By sizing the insert as described above, the resiliency of the insert material can be used to ensure a tight fit within the individual wells. A tight fit is useful in preventing accidental dislodging of the insert during shipping and handling. Thus, the inserts can be used in standard microtiter plates having smooth, substantially vertical walls. However, it is also possible to adapt microtiter plates specifically for use with inserts as described above by providing one or more inward projection in the inner surface of the well. An insert is used having a vertical height less than the vertical height of the well walls and the inward projection is placed just above the height of the insert, whereby the insert is locked into position when fully inserted into the well. A number of different types of projections can be used depending on the configuration of the insert. For example, if a cylindrical insert is used, a single small inward projection or a small number of small inward projections can be used to keep the cylinder in place. Such inward projections would only cover a small fraction of the inside circumference of the well wall and would be discontinuous. However, if a sheet only slightly longer in diameter than the diameter of the well is used (having only two contact points at the well walls) or a hollow polyhedron as described above is used (having three contact points for a prism, four contact points for a cube, etc.), it is preferred to utilize a continuous inward projection, such as a continuous ridge or ring, in order to avoid the problem of correctly registering the contact points with the inward projections.

In an alternative embodiment of the invention, an insert that does not fit completely within the well can be utilized. Inserts that project above the well walls are particularly suitable for applications in which the inserts are removed at various stages of processing the multiwell plate. Such inserts can either fit into individual wells or can be attached to one another so that they may be inserted into a plurality of wells at the same time. The connection between the various portions of the insert that fit into the individual wells is immaterial to the practice of the invention. However, most inserts will comprise an insert plate in which projections are formed. The insert plate will comprise one or more projections that fit into one or more of the wells of the multiwell plate. A preferred form for the projection is a hollow cylinder with open top and bottom surfaces, with the open cylinder projecting downward into the well from the insert plate. However, cylindrical inserts with closed tops and/or bottoms can also be used if the top and bottom surfaces transmit the beam of light either substantially without loss or with equal loss through all top and bottom surfaces (so that an equal change occurs in light transmitted in all wells, including control wells in which no reaction takes place). Projections with closed bottom surfaces in which the walls of the projection are nonporous and a microporous material is placed on the outer surface of the projection in the lower portion of the well offer the advantage of utilizing smaller volumes of liquid since liquid will be displaced upwardly by the projection as it is inserted into the well. Accordingly, fluid will surround and closely contact the microporous surface on the lower outer portion of the projection, and it will not be necessary to fill the well with a large volume of reagent liquid.

Although multiple, interconnected inserts which are removable can be used and then removed prior to transmission of light, it is also possible to lock the insert to the multiwell plate. Numerous methods for locking two contacting devices to each other are known in the art and need not be discussed here in detail. Examples include press fit connections, adhesives, spring clips, bolts, and the like. Preferred are locking devices which automatically engage when the projections are fully inserted into the wells.

Turning now to the figures, FIG. 1 is a plan view of a 4-well multiwell plate showing four different geometric arrangements of inserts. Four individual wells, indicated as 20(1) through 20(4) are seen in interconnecting horizontal plate 10. In this view from above, the bottom (30) of each well is seen. The vertical light beam location is indicated by the dashed circle surrounding the number 30. Four inserts (40) are seen in the individual wells, each insert being numbered 40(1) through 40(4) corresponding to the numbering system utilized for the individual wells.

Well 20(1) contains insert 40(1), which is in the shape of a hollow cube lacking top and bottom surfaces. The sides of insert 40 are selected so that each corner of the cube touches or closely approaches the inner vertical wall of well 20(1). A similar situation is seen in well 20(2), except that insert 40(2) is in the shape of a hollow prism lacking top and bottom surfaces.

Well 20(3) contains insert 40(3) in the shape of a sheet approximately equal in length to the circumference of well 20(3). Insert sheet 40(3) is therefore formed into the shape of a cylinder that fits tightly against the walls of well 20(3). In this embodiment, insert 40(3) is formed in two parts from layers of microporous material 50 and a resilient backing 60. The springiness of the resilient backing provides the force by which insert 40(3) is retained firmly within the well as it tries to spring back to its original flat shape.

Well 20(4) contains insert 40(4), which comprises a sheet of microporous surface material slightly longer than the diameter of well 20(4). The flexure of the sheet moves the central portion of the sheet away from the central portion of well 20(4), thereby allowing the light beam to pass undisturbed through well bottom 30. This embodiment requires that the microporous surface be either resilient or rigid or that the microporous surface be attached to a rigid or resilient backing material.

Figure 2:
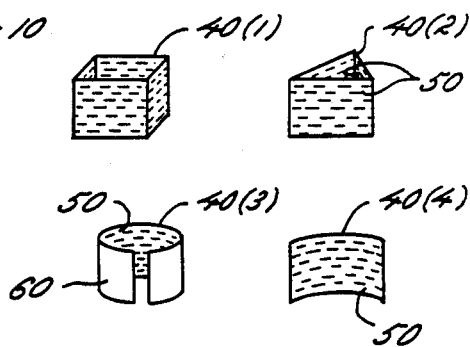
FIG. 2 is a series of perspective views showing the individual inserts from the wells of FIG. 1.

FIG. 2 is a series of perspective drawings of the inserts shown in FIG. 1. Insert 40(1) is in the form of a hollow cube lacking a top or bottom surface and comprises a microporous surface material without a backing. A similar configuration is seen for insert 40(2), except that the insert is in the form of a hollow prism rather than a hollow cube. Insert 40(3) is in the form of a hollow cylinder that fits just within the interior walls of the sample well. A resilient backing 60 provides springiness to hold the cylinder in place while the microporous surface 50 faces the interior of the well and provides a reaction surface. Insert 40(4) is a slightly arched sheet.

Figure 3A:
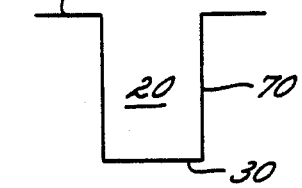
FIGS. 3 (a–c) are a series of vertical cross-sections showing different configurations for the vertical walls of individual wells.
Figure 3B:
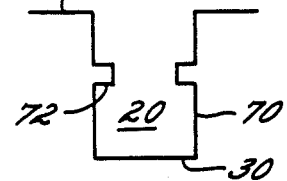
Figure 3C:
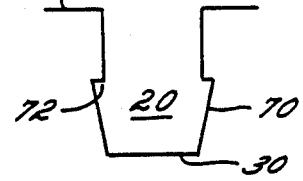

FIG. 3 is a series of vertical cross-sectional views showing microtiter plate wells. Well 20 has a transparent bottom surface 30 which is attached through continuous vertical walls 70 to plate 10 which interconnects the plurality of sample wells (not shown). In FIG. 3A, vertical walls 70 are smooth and continuous. In the embodiment shown, walls 70 are exactly vertical. It is possible to have these walls be merely substantially vertical; for example, the diameter of the well at the top of the well can be slightly greater than or slightly less than the diameter at the bottom of the well. FIG. 3B shows a well 20 with a bottom 30 and vertical walls 70 connected to horizontal plate 10. An inward projection 72 in the form of a raised ring around the inner circumference of the well 20 is present in well 70. In this vertical cross-section, the inwardly projecting ring can be seen at two locations opposite each other. The height of the inward projection above the bottom surface 30 of the well is selected to be slightly larger than the height of an insert of the type shown in FIG. 2. Inwardly projecting ring 72 thus acts as a retaining ring. As shown in FIG. 3C, inward projection 72 need not be a raised ring or other raised projection in vertical wall 70 but may represent a narrowing of the diameter of well 20 near the top of the wall.

Figure 4:
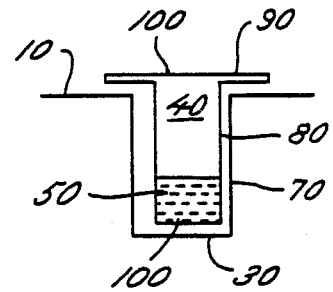
FIG. 4 is a cross-sectional view of a single well containing a removable insert that does not fit completely within the well.

FIG. 4 shows a removable insert that does not fit completely within well 20. In the embodiment shown, insert 40 comprises a horizontal plate 90 that fits over plate 10 in which well 20 is formed. A projection 80 extends below plate 90 into the lower region of well 20 near bottom surface 30. A microporous surface 50 is present on the lower portion of projection 80 in the region of well 20 in which liquid will be present. The embodiment shown has upper and lower surfaces 100 of insert 40, which may or may not transmit light. In embodiments in which upper and lower surfaces 100 do not transmit light or transmit light altered by passage through the surfaces, the insert can be removed prior to reading the transmission of light through the reaction fluid in well 20. By providing the insert in a removable form, it is considered to be shaped to fit the well without interfering with passage of a vertical beam of light. However, insert 40 can be manufactured from a transparent material so that upper and lower surfaces 100 transmit light substantially unchanged, in which case there is no need to remove the insert prior to reading transmittance.

Figure 5:
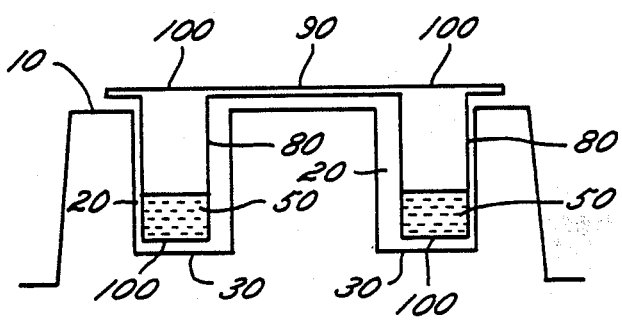
FIG. 5 is a cross-sectional view of a multiple-projection insert in which projections fit into two adjacent wells of a multi-well plate.

FIG. 5 shows an embodiment of the invention similar to that present in FIG. 4 but in which a plurality of projections 80 are connected by a horizontal plate 90. Each of the projections 80 extends into one of the wells 20 that are formed in plate 10. As in FIG. 4, projections 80 contain a lower portion having a microporous surface 50. FIG. 5, in contrast to FIGS. 3 and 4 which showed only the region of plate 10 adjacent to well 20, shows a complete cross-section of plate 10 including vertical extensions 12 that extend downward from horizontal plate 10 to form the base on which the plate rests.

Figure 6:
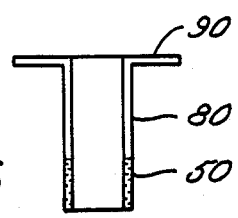
FIG. 6 is a cross-sectional view of a hollow cylindrical insert.

FIG. 6 is a vertical cross-section of an insert of the invention in which projection 80 is in the form of a hollow cylinder attached to plate 90. The lower portion of projection 80 is either formed from hydroporous material 50 or has hydroporous material 50 coated on its surface. The insert shown in FIG. 6 is similar to the insert shown in FIG. 4 but does not have upper or lower surfaces through which light passes. Hollow cylinders can also be prepared in multiple cylindrical inserts joined by a plate in analogy to FIG. 5.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A multiwell plate suitable for use in a spectrophotometer which uses a vertical beam of light comprising:
   a first plate having a plurality of wells for receiving sample, wherein said wells have transparent bottom surfaces to allow for the transmission of a vertical beam of light;
   a unitary insert comprising a biochemically compatible microporous binding surface shaped to fit into at least one well of said plate without interfering with said vertical beam of light so as to provide a free light path through said well, said free light path passing through said sample when said sample is present in said well.

2. The multiwell plate of claim 1, wherein said insert comprises a second plate arranged to fit over said first plate and having one or more projections which fit into said one or more of said wells.

3. The multiwell plate of claim 2, wherein said projections comprise hollow cylinders with open top and bottom surfaces.

4. The multiwell plate of claim 2, wherein said projections comprise cylinders with a top or bottom surface through which said beam of light is transmitted substantially without loss.

5. The multiwell plate of claim 2, wherein said insert is removable.

6. The multiwell plate of claim 2, wherein said second plate locks to said first plate when said projection is fully inserted into said well.

7. The multiwell plate of claim 2, wherein said insert comprises a sufficient number of projections to fit into all of said wells.

8. The multiwell plate of claim 2, wherein said insert comprises a single projection which fits into a single well.

9. The multiwell plate of claim 1, wherein said insert fits completely within said well.

10. The multiwell plate of claim 9, wherein said insert comprises a sheet of microporous material longer than the diameter of said well.

11. The multiwell plate of claim 10, wherein said sheet is substantially equal in length to the circumference of said well and said sheet fits against the vertical walls of said well.

12. The multiwell plate of claim 9, wherein said insert comprises a hollow polyhedron without a top or bottom surface.

13. The multiwell plate of claim 12, wherein said polyhedron is a triangular prism.

14. The multiwell plate of claim 9 wherein said insert fits within the bottom two-thirds of said well.

15. The multiwell plate of claim 14, wherein said well comprises substantially vertical walls and said vertical walls comprise an inward projection above the height of said insert, whereby said insert is locked into position in said well.

16. The multiwell plate of claim 9, wherein said microporous surface comprises polyamide affixed to a flexible backing sheet.

17. The multiwell plate of claim 16, wherein said backing sheet is resilient.

18. The multiwell plate of claim 9, wherein said insert is irremovably attached to said well.

19. The multiwell plate of claim 9, wherein said insert is removably located within said well.

20. The multiwell plate of claim 1, wherein said microporous surface comprises polyamide.

* * * * *